United States Patent [19]

Havera et al.

[11] 4,181,657
[45] Jan. 1, 1980

[54] 2-AMINOOCTAHYDROINDOLO[2,3-A]QUINOLIZINES USEFUL IN TREATING CARDIOVASCULAR DISORDERS

[75] Inventors: Herbert J. Havera, Edwardsburg, Mich.; Horacio Vidrio, Mexico City, Mexico; Richard D. Johnson, Elkhart, Ind.

[73] Assignee: Miles Laboratories, Inc., Elkhart, Ind.

[21] Appl. No.: 924,622

[22] Filed: Jul. 14, 1978

[51] Int. Cl.² ................ A61K 31/445; C07D 471/04
[52] U.S. Cl. .......................................... 424/256; 546/70
[58] Field of Search ............. 260/293.53, 293.55; 424/262, 256; 546/70

[56] References Cited

U.S. PATENT DOCUMENTS 3,962,258  6/1976  Archibald et al. ............. 260/293.61

FOREIGN PATENT DOCUMENTS 233085  3/1959  Australia ............................ 260/293.53
102805  10/1965 Denmark ............................ 260/293.53

OTHER PUBLICATIONS

Schellenberg, K., *J. Org. Chem.,* 28, 3259–3261 (1963).

*Primary Examiner*—Alan L. Rotman
*Assistant Examiner*—Richard A. Schwartz
*Attorney, Agent, or Firm*—Richard W. Winchell

[57] ABSTRACT

Novel compounds having the structural formula

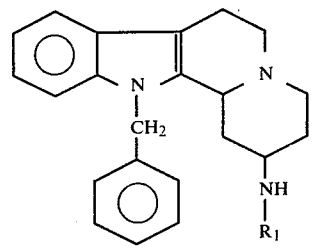

wherein $R_1$ is hydrogen, i-propyl, phenyl or a substituted phenyl having the structure

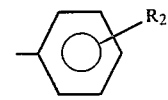

wherein $R_2$ is halogen, methoxy, lower alkyl, nitro, trifluoromethyl, acetamido, or sulfonamido and their acid addition salts, are useful for treatment of cardiovascular disorders such as cardiac arrhythmia, hypertension, and angina pectoris. Methods for preparation and use of these compounds are described.

16 Claims, No Drawings

2-AMINOOCTAHYDROINDOLO[2,3-a]QUINOLIZINES USEFUL IN TREATING CARDIOVASCULAR DISORDERS

BACKGROUND AND PRIOR ART

There are several clinical cardiovascular disorders, including angina pectoris, arrhythmia, and hypertension, among others. Compounds suitable for treatment of any of these conditions would find therapeutic use. Certain quinolizine derivatives have utility for these purposes. See, for example, U.S. Pat. Nos. 3,536,725 and 3,087,930.

A starting material in the preparation of compounds described in the present application, 12-benzyl-1,2,3,4,6,7,12,12b-octahydro-2-oxo-indolo[2,3a]quinolizine, has been disclosed by Novak and Szantay (Chem. Ber. 102, 3959 (1969); hereinafter NOVAK), who stated no utility for the compound. Archibald et al. (U.S. Pat. No. 3,962,258; hereinafter ARCHIBALD) specifically disclose the compound having the Formula,

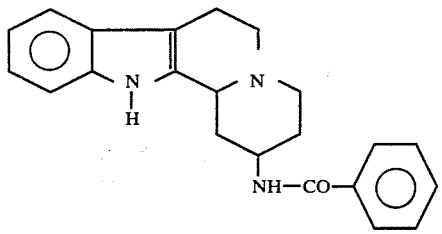

and broadly disclose compounds having the Formula,

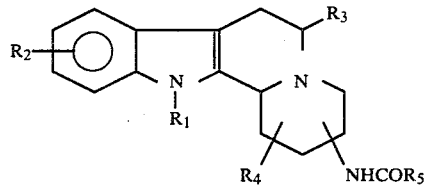

wherein
R₁ is hydrogen, alkyl, aralkyl, or aroyl;
R₂ is hydrogen, halogen, alkoxy, hydroxyl, or alkyl;
R₃ is hydrogen, hydroxyl, alkyl, or oxo;
R₄ is hydrogen, halogen, or alkyl;
R₅ is benzyl, cyclohexyl, phenyl, or phenyl substituted by halogen, alkoxy, or alkyl.

ARCHIBALD stated that these compounds possess hypotensive activity and anti-histamine activity when tested on warm blooded animals.

SUMMARY OF THE INVENTION

The subject matter of this invention includes:
(1) A compound having Formula I,

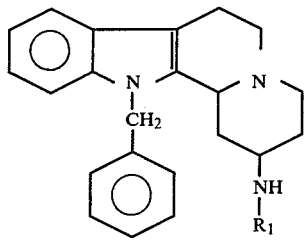

wherein R₁ is hydrogen, i-propyl, phenyl or a substituted phenyl having the structure

wherein R₂ is halogen, methoxy, lower alkyl, nitro, trifluoromethyl, acetamido, or sulfonamido; and acid addition salts thereof;

(2) A process for preparing a compound having Formula I comprising:
(a) reacting 12-benzyl-1,2,3,4,6,7,12,12b-octahydro-2-oxo-indolo [2,3a] quinolizine, having Formula II,

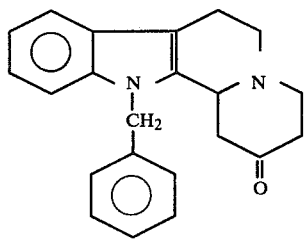

with an amino compound under acidic conditions to produce an imino compound having Formula III,

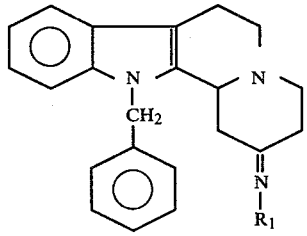

(b) reducing the imino compound having Formula III; (3) A therapeutic method of treating cardiac arrhythmia in an individual for whom such therapy is indicated, comprising administering to the individual a therapeutically effective amount of a compound selected from the group consisting of 2-anilino-12-benzyl-1,2,3,4,6,7,12,12b-octahydroindolo [2,3a]quinolizine; 12 benzyl-2-(3-nitroanilino)-1,2,3,4,6,7,12,12b-octahydroindolo[2,3a]quinolizine; 12-benzyl-2-(3-bromoanilino)-1,2,3,4,6,7,12,12b-octahydroindolo[2,3a] quinolizine; 12-benzyl-2-(4-bromoanilino)-1,2,3,4,6,7,12,12b-octahydroindolo [2,3a] quinolizine; 12-benzyl-2-isopropylamino-1,2,3,4,6,7,12,12b-octahydroindolo 2,3a quinolizine; 2-amino-12 benzyl-1,2,3,4,6,7,12,12b-octahydroindolo[2,3-a]quinolizine and the acid addition salts thereof; (4) A therapeutic method of treating hypertension in an individual for whom such therapy is indicated, comprising administering to the individual a therapeutically effective amount of a compound selected from the group, consisting of 12-benzyl-2-(4-methoxyanilino)-1,2,3,4,6,7,12,12b-octahydroindolo[2,3a]quinolizine; 12-benzyl-2-(3-methylanilino)-1,2,3,4,6,7,12,12b-octahydroindolo[2,3-a]quinolizine; 2-(4-acetamidoanilino)-12-benzyl-1,2,3,4,6,7,12,12b-octahydroindolo[2,3-a]quinolizine; 2-(3-acetamidoanilino)-12-benzyl-1,2,3,4,6,7,12,12b-octahydroindolo[2,3-a]quinolizine; 12-benzyl-1,2,3,4,6,7,12,12b-octahydro-2-(4-sulfonamidoanilino)-indolo[2,3-a]quinolizine; and the acid addition salts thereof; (5) A therapeutic method of treating angina pectoris in an individual for whom such therapy is indicated, comprising administering to the individual a therapeutically effective amount of a compound having the Formula given in part (1) above.

DESCRIPTION OF THE INVENTION

The novel compounds having Formula I are the subject of this invention.

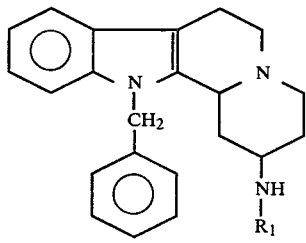

I.

In compounds having Formula I, $R_1$ is hydrogen, i-propyl, phenyl or a substituted phenyl having the structure

wherein $R_2$ is halogen, methoxy, lower alkyl, nitro, trifluoromethyl, acetamido, or sulfonamido.

The invention also includes pharmacologically acceptable acid addition salts of compounds having Formula I. Such salts are prepared from suitable acids, such as hydrochloric, hydrobromic, maleic, fumaric, or the like. These salts are prepared by reacting compounds having Formula I with at least one equivalent of acid in a water-polar organic solvent mixture, such as water and ethanol.

The compounds and salts of this invention possess unexpected pharmacological properties that render them useful as therapeutic agents for the treatment of cardiovascular disorders, such as cardiac arrhythmia, hypertension, and angina pectoris in an individual for whom such therapy is indicated. The term "individual" means a human being or an experimental animal that is used as a model for a human being. The effective dose may vary from individual to individual, but it is easily determined by one skilled in the art without undue experimentation. Dose forms for the administration of compounds having Formula I may be prepared by recognized methods of the pharmaceutical sciences. Various dose forms of compounds having Formula I may be administered by conventional methods of therapeutic administration, such as oral, intravenous, parenteral, or the like.

Compounds of this invention are prepared from the starting compound 12-benzyl-1,2,3,4,6,7,12,12b-octahydro-2-oxo-indolo[2,3-a]quinolizine, prepared as described by NOVAK, and having Formula II.

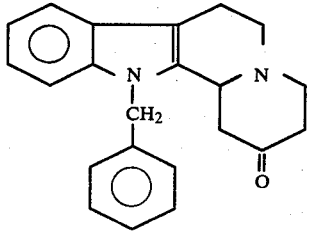

II.

A compound having Formula II is then reacted with an amino compound under acidic conditions to produce an imino compound having Formula III.

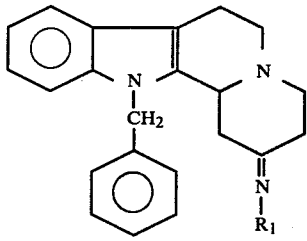

III.

Preferred amino compounds suitable for this reaction include hydroxylamine, isopropylamine, aniline and substituted aniline compounds having the Formula

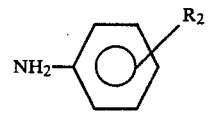

wherein $R_2$ is a halogen, methoxy, lower alkyl, nitro, trifluoromethyl, acetamido, or sulfonamido group. Lower alkyl is defined as an alkyl group having 1 to 3 carbon atoms. The $R_2$ substituent may be located in any position from $C_2$ to $C_5$ on the phenyl ring. In the preferred mode of the invention the $R_2$ substituent is located at the $C_3$ or $C_4$ position on the phenyl ring. Most preferred aniline derivatives, to be considered as illustrating but not limiting the scope of this invention, include aniline, 3-nitroaniline, 4-methoxyaniline, 3-methylaniline, 3-bromoaniline, 4-bromoaniline, 3-trifluoromethylaniline, 4,acetamidoaniline, 3-acetamidoaniline, and 4-sulfonamidoaniline.

The reaction is performed in a suitable solvent, such as methanol, toluene, dimethylformamide (DMF) or the like at a temperature of from about 0° C. to the reflux temperature of the solvent, and may require from about 1 to 24 hours for completion. The reaction mixture may be made acidic by a suitable organic or inorganic acid, such as p-toluenesulfonic acid, hydrochloric acid or sulfuric acid. Preferred reaction conditions provide for the removal of water, a by-product of the reaction, to drive the reaction to completion. This may be done by the means of distillation or the addition of water-trapping molecular sieves to the reaction mixture. As an example of the most preferred conditions, toluene is used as the solvent, the reaction is maintained at reflux temperature, and the water is distilled off and collected and measured in a Dean-Stark trap to determine when the theoretical amount of water has been produced and the reaction is complete.

It is not necessary to isolate the imino product having Formula III, since it may be reduced in situ. Preferably, however, when the water is removed from the reaction mixture, the product of Formula III is isolated by removal of the solvent before proceding to the reduction step below.

The imino compound having Formula III is reduced by means of a suitable reducing agent to give a compound having Formula I. The reducing agent may be one of several widely known in the art, such as hydrogen in the presence of a catalyst, an alkali metal hydride, an alkali metal borohydride, or an organoborohydride. We prefer to use one of the hydrides mentioned. Examples of most preferred reducing agents are sodium borohydride and any suitable organic solvent, such as methanol, toluene, DMF, or the like. The temperature is preferably held at about 0° C. to 20° C. initially and then raised to from 20° C. to reflux temperature, such that the total reaction time is from about 3 to 72 hrs., preferably 3–8 hrs.

In the following examples, Compound II is the starting material, 12-benzyl-1,2,3,4,6,7,12,12b-octahydro-2-oxo-indolo [2,3-a]-quinolizine prepared as described by NOVAK.

EXAMPLE 1

Preparation of
2-anilino-12-benzyl-1,2,3,4,6,7,12,12b-octahydroindolo[2,3-a]quinolizine dihydrochloride (TR2981)

A solution of freshly distilled aniline (17 g, 0.18 mole) in 100 ml of absolute methanol was stirred in an ice-bath and 33 ml of 2.78 N HCl in methanol (0.09 mole) was added slowly. Then 10 g (0.03 mole) of Compound II was added. The resulting mixture was allowed to stir at about 18° C. for 72 hours. The reaction mixture was then rendered strongly acidic by the careful addition of concentrated HCl. The solvent was evaporated in vacuo on the steam bath to leave a residue to which was added equal parts of 20% NaOH and chloroform until the aqueous layer became alkaline. The mixture was stirred until dissolution occurred. The resulting layers were separated and the aqueous layer further extracted with chloroform. The combined chloroform extracts were dried over $MgSO_4$ and then evaporated in vacuo to give a yellow oil. The yellow oil was dissolved in 80 ml of hot 2-propanol to yield 9.6 g (78.7%) of the free base, mp 148°–150° C. A sample of the free base was dissolved in a hot mixture of methanol-chloroform and 10 ml of a solution of 2.49 N HCl in 2-propanol was added. The resulting solution was concentrated and cooled. A white solid which crystallized was removed by filtration, washed with cold 2-propanol and dried to give 4 g of Compound TR-2981, mp 259°–260° dec.

Anal. Calc'd for $C_{28}H_{31}Cl_2N_3$: C, 69.99; H, 6.50; N, 8.74. Found: C, 69.85; H, 6.52; N, 8.73.

EXAMPLE 2

Preparation of
12-benzyl-2-(3-nitroanilino)-1,2,3,4,6,7,12,12b-octahydroindolo[2,3-a]quinolizine (TR-2998)

The procedure of Example 1 was repeated, substituting 3-nitroaniline (24.9 g, 0.18 mole) for aniline. Compound TR-2998 (8.7 g, 64%) was isolated as the free base, instead of as the hydrochloride salt and was obtained as a yellow solid, mp 189°–190° C.

Anal.: Calc'd for $C_{28}H_{28}N_4O_2$: C, 74.31; H, 6.23; N, 12.38. Found: C, 74.19; H, 6.33; N, 12.32.

EXAMPLE 3

Preparation of
12-benzyl-2-(4-methoxyanilino)-1,2,3,4,6,7,12,12b-octahydroindolo[2,3-a]quinolizine dihydrochloride (TR-3006)

The procedure of Example 1 was repeated, substituting 4-methoxyaniline (22.2 g, 0.18 mole) for aniline. However, after the reaction solvent was evaporated in vacuo, the oil which remained was distilled in vacuo to remove excess 4-methoxyaniline as a pale yellow oil (bp 71°/0.4 mm). The residue in the distillation vessel was then stirred in 400 ml of ether and filtered to remove a small amount of insoluble residue. The ether solution was cooled in an ice-bath and 50 ml of 2.78 N HCl in methanol was added. An oil formed and the mixture was heated with stirring on the steam bath to drive off excess HCl and solvent. The oil crystallized as the solvent evaporated. The crystals were boiled with methanol, collected and air dried to yield 9.3 g (60.7%) of Compound TR-3006, mp 256°–258° dec.

Anal.: Calc'd for $C_{29}H_{33}Cl_2N_3O$: C, 68.23; H, 6.51; N, 8.23. Found: C, 67.61; H, 6.36; N, 8.061

EXAMPLE 4

Preparation of
12-benzyl-2-(3-methylanilino)-1,2,3,4,6,7,12,12b-octahydroindolo[2,3-a]quinolizine dihydrochloride (TR-3008).

The procedure of Example 1 was repeated, substituting 3-methylaniline (19.3 g, 0.18 mole) for aniline. However, after the chloroform extract was evaporated, an oil remained which was distilled in vacuo to remove excess 3-methylaniline as a colorless liquid (8 g, bp 30°/0.035 mm). The residue in the distillation vessel was dissolved in 500 ml of ether and cooled in an ice-bath as 50 ml of 2.78 N HCl in methanol was carefully added, whereupon an oil separated from the solution. The solvent was then evaporated in vacuo and the oil which remained was crystallized from a mixture of methanol and ethyl acetate to give 16.2 g of a solid. The solid was crystallized from acetone and chloroform; the crystals were removed by filtration to yield 4.2 g (28.3%) of Compound TR3008, mp 250° dec. (28.3%).

Anal.: Calc'd for $C_{29}H_{33}Cl_2N_3$: C, 70.44; H, 6.72; N, 8.50. Found: C, 69.55; H, 6.70; N, 8.42.

EXAMPLE 5

Preparation of
12-benzyl-2-(3-bromoanilino)-1,2,3,4,6,7,12,12b-octahydroindolo[2,3-a]quinolizine hydrochloride (TR-3014).

The procedure of Example 1 was repeated, substituting 3-bromoaniline (31 g, 0.18 mole) for aniline. However, after the chloroform extract was evaporated, an oil remained which was distilled in vacuo to remove excess 3-bromoaniline as a yellow oily liquid (24.6 g, bp 56°/0.075 mm). The residue in the distillation vessel was stirred for 3 hr with 400 ml of hot 3 N HCl; then stirred at room temperature for an additional 20 hr during which a solid separated from the solution. The solid was removed by filtration and was recrystallized from aqueous MeOH to give 12 g (76.4%) of Compound TR-3014 mp 261°–264° (dec.).

Anal.: Calc'd for $C_{28}H_{29}BrClN_3$: C, 64.31; H, 5.59; N, 8.03. Found: C, 64.54; H, 5.57; N, 8.11.

EXAMPLE 6

Preparation of 12-benzyl-2-(4-bromoanilino)-1,2,3,4,6,7,12,12b-octahydroindolo[2,3-a]quinolizine dihydrochloride (TR-3631).

To 9.6 g (0.029 mole) of Compound II in 100 ml of dry toluene was added 5.0 g (0.029 mole) of 4-bromoaniline and a trace of p-toluenesulfonic acid. The reaction mixture was heated to reflux for 18 hr and a Dean-Stark trap was used to collect 0.5 ml. of water. The solvent was evaporated in vacuo and an oily residue remained (IR 1650 cm$^{-1}$, imine). The oily residue was suspended in 100 ml of methanol and 50 ml of DMF. The solution was cooled in an ice bath and 3.4 g (0.09 mole) of NaBH$_4$ was added carefully thereto with stirring. The solution was stirred for 1 hr in the cold, then heated to reflux for 2 hr. Water was then added and the solution was concentrated in vacuo to leave an oily residue which was chromatographed over 600 g of silica gel eluting with a benzene, ethyl acetate mixture (1:1 V/V) and then ethyl acetate. There was obtained 5.0 g of pure amine. The dihydrochloride was prepared by adding 4 ml of a 4.96 N HCl solution in 2-propanol to the free base in methanol. A precipitate formed which was recrystallized from aqueous methanol, yield 3.5 g of Compound TR-3631, mp 275°–76°.

Anal.: Calc'd for $C_{28}H_{30}BrCl_2N_3$: C, 60.12; H, 5.40; N, 7.57. Found: C, 60.15; H, 5.51; N, 7.57.

EXAMPLE 7

Preparation of 12-benzyl-1,2,3,4,6,7,12,12b-octahydroindolo-2-(3-trifluoromethylanilino)[2,3-a]quinolizine dihydrochloride (TR-3633)

The procedure of Example 6 was repeated using 3-trifluoromethylaniline in place of 4-bromoaniline. There was obtained 5.0 g of pure amine. The dihydrochloride was prepared by adding 4.7 ml of 4.96 N HCl in 2-propanol to the free base in methanol. Upon addition of ether, a solid precipitated which was recrystallized from methanol and ether, yield 3.5 g of Compound TR-3633, mp 207°–208°.

Anal.: Calc'd for $C_{29}H_{30}Cl_2F_3N_3$: C, 63.50; H, 5.51; N, 7.66. Found: C, 63.28; H, 5.54; N, 7.74.

EXAMPLE 8

Preparation of 2-(4-acetamidoanilino)-12-benzyl-1,2,3,4,6,7,12,12b-octahydroindolo-[2,3-a]quinolizine dihydrochloride (TR-3635).

The procedure of Example 6 was repeated using 4-aminoacetaniline in place of the 4-bromoaniline. Instead of chromotographing the oily residue, it was extracted with chloroform. The chloroform was dried over MgSO$_4$ and concentrated in vacuo leaving 5.5 g of a solid. The dihydrochloride was prepared by adding 5 ml of a 4.96 N HCl solution in 2-propanol to the free base in methanol. Upon addition of ether, a precipitate formed which was recrystallized from aqueous methanol and ether, yield 3.5 g of Compound TR-3635, mp 269°–270°.

Anal.: Calc'd for $C_{30}H_{34}Cl_2N_4O$: C, 67.03; H, 6.37; N, 10.42. Found: C, 66.74; H, 6.22; N, 10.46.

EXAMPLE 9

Preparation of 12-benzyl-2-isopropylamino-1,2,3,4,6,7,12,12b-octahydroindolo[2,3-a]quinolizine dihydrochloride monohydrate (TR-3687)

To 8.9 g (0.027 mole) of Compound II in 200 ml of dry benzene was added 2.0 g (0.039 mole) of isopropylamine, a trace of p-toluenesulfonic acid and 35 g of 5 A molecular sieves. The solution was shaken on a Paar apparatus for 20 hr. The solution was filtered and the filtrate was concentrated in vacuo leaving 10 g of an oil. The oil was suspended in 50 ml of methanol, cooled in an ice bath and 2.0 g (0.054 mole) of NaBH$_4$ was carefully added to the solution with stirring. The solution was stirred in the cold for 2 hrs and heated to reflux for 1 hr. The solution was concentrated in vacuo and the residue was dissolved in chloroform. The chloroform was dried over MgSO$_4$ and concentrated in vacuo leaving 7 g of an oil. The oil was chromatographed over silica gel eluting first with benzene followed by a mixture of ethyl acetate and CH$_3$OH (1:1 V/V). There was obtained 6.0 g of free amino. The dihydrochloride was prepared by adding 9.37 ml of a 3.43 N HCl solution in 2-propanol to the free base in methanol. Upon addition of ether a solid precipitated which was recrystallized from a methanol-ether mixture; yield 2.0 g of Compound TR-3687, mp 284°–85°.

Anal.: Calc'd for $C_{25}H_{35}N_3Cl_2O$: C, 64.64; H, 7.59; N, 9.04; Cl, 15.27; O, 3.44. Found: C, 64.71; H, 7.08; N, 8.97; Cl, 15.24; O, 3.75.

EXAMPLE 10

Preparation of 2-amino-12-benzyl-1,2,3,4,6,7,12,12b-octahydroindolo[2,3-a]-quinolizine dihydrochloride monohydrate (TR-3698).

To 8.9 g (0.027 mole) of Compound II was added 2.9 g (0.042 mole) of hydroxylamine hydrochloride in 20 ml of pyridine and 20 ml of ethanol. The solution was heated to reflux for 2 hrs with stirring. The solution was concentrated in vacuo leaving a solid to which was added aqueous NH$_4$OH and the alkaline solution was extracted with chloroform. The chloroform was dried over MgSO$_4$ and concentrated in vacuo leaving 9.0 g of an oil. To the oil was added a solution of diborane prepared from 10 g of BF$_3$ and 5 g of NaBH$_4$ in 150 ml of tetrahydrofuran. The solution was heated to reflux with stirring for 3 hr. The mixture was cooled and 20% HCl was carefully added until acidic. The solution was concentrated in vacuo and made basic with 20% NaOH. The organic material was extracted with chloroform. The chloroform was dried over MgSO$_4$ and concentrated in vacuo leaving 9.0 g of an oil. The dihydrochloride was prepared by adding 15.8 ml of 3.43 N HCl solution in 2-propanol to the free base in methanol. Upon addition of ether, a gummy material was obtained which was recrystallized from aqueous methanol and ether to yield 2.0 g of Compound TR-3698 mp > 290.

Anal.: Calc'd. for $C_{22}H_{29}Cl_2N_3O$: C, 62.55; H, 6.94; N, 9.94. Found: C, 62.44; H, 6.86; N, 9.96.

EXAMPLE 11

Preparation of 2-(3-acetamidoanilino)-12-benzyl-1,2,3,4,6,7,12,12b-octahydroindolo[2,3-a]quinolizine oxalate (TR-3716).

The procedure of Example 6 was repeated using 3-aminoacetanilide in place of 4-bromoaniline. By chromatography, 10 g of free base was obtained. The oxalate was prepared by adding 1.94 g (0.024 mole) of oxalic acid to the 10 g of free base in methanol. Upon addition of ether, a gummy solid separated, which was recrystallized from aqueous methanol to yield 6.0 g of Compound TR-3716, mp 175°–178°.

Anal.: Calc'd. for $C_{32}H_{34}N_4O_5$: C, 69.29; H, 6.18; N, 10.10. Found: C, 69.82; H, 6.12; N, 10.09.

EXAMPLE 12

Preparation of 12-benzyl-1,2,3,4,6,7,12,12b-octahydro-(4-sulfonamidoanilino)-indolo[2,3-a]quinolizine hydrochloride (TR-3718)

The procedure of Example 6 was repeated using sulfanilamide in place of 4-bromoaniline. The free base was converted to the hydrochloride by adding 1.6 ml of 4.55 N HCl solution in 2-propanol to 3.5 g of free base in methanol. Upon addition of ether, a gummy material formed which was recrystallized from a methanol-ether mixture to yield 1.5 g of Compound TR-3718, mp 268°–270°.

Anal.: Calc'd. for $C_{28}H_{31}ClN_4O_2S$: C, 64.29; H, 5.97; N, 10.71. Found: C, 63.84; H, 5.88; N, 10.41.

EXAMPLE 13

BIOLOGICAL SCREENING

Compounds of this invention were tested in the following animal studies for biological activity:
(a) Antiarrhythmic Activity
(b) Antihypertensive Activity
(c) Antianginal Activity

A. Evaluation of Antiarrhythmic Activity

The antiarrhythmic activity of the compounds of this invention was determined in the experimental model described by J. W. Lawson (J. Pharmacol. Exper. Therap. 160:22–31, 1968). Test compounds were administered to groups of 5 mice at an intraperitoneal dose of 31 mg/kg. Ten minutes after injection each mouse was placed in a covered 300 ml glass beaker which contained cotton saturated with chloroform. The animal was observed closely and removed from the beaker immediately after respiratory arrest. The heart was quickly exposed by making an incision through the abdomen, diaphragm, thorax and pericardium for visual inspection of ventricular rate and rhythm. Ventricular contractions were counted for 30 seconds and animals with a rate not exceeding 100 beats per 30 seconds were considered protected from the ventricular arrhythmia produced by chloroform. Compounds protecting at least 3 of the 5 mice were subsequently tested at various doses and the results obtained were used to calculate the mean effective doses (ED50) and 95% confidence limits after the method of Litchfield and Wilcoxon (J. Pharmacol. Exper. Therap. 96:99–113, 1949). Table A presents the results obtained in the antiarrhythmic study.

TABLE A

Antiarrhythmic Activity of Indoloquinolizines in the Mouse

| Compound | ED50 (95% C.L.) mg/kg, i.p. |
|---|---|
| TR2981 | 31 (14–68) |
| TR2998 | 12 ( 5–13) |
| TR3006 | * |
| TR3008 | * |
| TR3014 | 32 (16–66) |
| TR3631 | 37 (23–60) |
| TR3633 | * |
| TR3635 | * |
| TR3687 | 19 (12–30) |
| TR3698 | 42 (24–73) |
| TR3716 | * |
| TR3718 | * |

*Did not protect 3 of 5 mice and thus was not tested further.

Explanations and conclusions regarding Table A. Compounds TR2981, TR2998, TR3014, TR3631, TR3687, and TR3698 protected at least 3 of 5 mice at the 31 mg/kg dose level, thus establishing the usefulness of these compounds as antiarrhemic agents. Subsequent testing at additional dose levels established mean effective dose levels useful for treatment of arrythmia ranging from 12 to 42 mg/kg.

B. Evaluation of Antihypertensive Activity

Rats were made hypertensive by applying a figure of eight ligature to one kidney and removing the contralateral kidney two weeks later. At least four weeks after the second operation the animals were subjected to indirect systolic blood pressure measurements with an occluding cuff and pulse sensor system applied to the tail. Pressure measurements were made before and 1,2,4,6 and 8 hours after oral administration of the test compounds at a dose of 31 mg/kg. Each compound was tested in 5 or 10 rats. Statistical significance of differences between control and post treatment values was determined by Wilcoxon's signed rank test (F. Wilcoxon and R. A. Wilcox, Some Rapid Approximate Statistical Procedures, Lederle Laboratories, Pearl River, 1964). The results of this study are presented in Table B.

TABLE B

Antihypertensive Activity of Indoloquinolizines in the Rat. Test Dose: 31 mg/kg p.o.

| Compound | Number of Rats | Initial BP, mmHg | Change in Systolic Blood Pressure, mmHg, at | | | | |
|---|---|---|---|---|---|---|---|
| | | | 1 hr | 2 hr | 4 hr | 6 hr | 8 hr |
| TR2981 | 5 | 176 | −2 | +5 | −5 | +7 | +16* |
| TR2998 | 10 | 201 | 0 | −2 | −4 | 0 | −4 |
| TR3006 | 10 | 212 | −28* | −20* | −18* | −12 | −14 |
| TR3008 | 10 | 191 | −27* | −24* | −17* | −17* | −20* |
| TR3014 | 5 | 202 | +1 | −16 | −2 | 0 | −3 |
| TR3631 | 5 | 195 | +10* | −5 | +12 | +3 | 0 |
| TR3633 | 5 | 186 | −10 | +2 | +8 | +4 | +13 |
| TR3635 | 10 | 201 | −23* | −23* | −27* | −16 | −10 |
| TR3687 | 5 | 194 | −2 | +16 | +18* | +18 | +9 |
| TR3698 | 5 | 194 | −4 | −11 | −3 | +14 | +3 |
| TR3716 | 10 | 204 | −49* | −42* | −28* | −17* | −6 |
| TR3718 | 10 | 206 | −5 | −16 | −21* | −5 | +5 |

*Statistically significant change from control.

C. Evaluation of Antianginal Activity

Angina pectoris is a clinical condition of hypoxia that results from an imbalance in myocardial oxygen supply and demand. A drug reducing oxygen demand is useful in the treatment of angina pectoris, as has been the case with nitroglycerin and the beta-adrenergic blocking agents like propranolol (J. R. Paratt, Advan. Drug Res. 9:103-134, 1974). Accordingly, the antianginal activity of 2-substituted indoloquinolizines was evaluated by assessing their capacity to reduce oxygen consumption by the dog heart in situ. This method allows measurement of the difference in oxygen content of the arterial and venous blood.

Mongrel dogs were anesthetized with pentobarbital and cannulas inserted in the trachea and in a femoral vein for artificial respiration with room air and for injection of test compounds, respectively. Heparin was administered intravenously to prevent blood clotting. The chest was opened at the sternal midline and an additional cannula introduced in the coronary sinus. Samples of blood were obtained from the coronary sinus cannula and from the thoracic aorta by direct puncture of the vessel. Partial pressure of oxygen in the samples was determined with a blood gas analyzer. Test compounds were injected intravenously at a dose of 1 mg/kg; oxygen measurements were made before administration and at 1, 5, 10, 20, 30, 40, 50 and 60 min after administration. One animal was used per test compound. As the standard of comparison, nitroglycerin was administered to a test animal and measurements were made in a similar manner.

Differences between partial pressure values in arterial and venous blood samples were calculated for each measurement. Since coronary sinus blood is representative of the venous effluent from the heart, these differences reflect the consumption of oxygen by the myocardium. Thus, the decrease in arteriovenous oxygen difference produced by the compounds by this invention indicates a reduction in myocardial oxygen consumption.

Table C presents the results obtained in the antianginal study.

Explanation and conclusions regarding Table C. In this procedure, the differences in arterio-venous oxygen consumption tend to increase with time in control animals by a maximum of 15%. Thus any drug-induced decrease in such differences can be regarded as significant. Nitroglycerin is regarded as the only acute acting drug for which antianginal activity is undisputed.

Thus, based upon comparison with nitroglycerin, antianginal activity is seen with all the test compounds, and particularly with compounds TR2981, TR2998, TR3006, TR3014, TR3631, TR3633, and TR3687.

SIGNIFICANCE OF BIOLOGICAL SCREENING RESULTS

The usefulness of the compounds of this invention in the treatment of cardiovascular disorders may be seen in the fact that the compounds are active as antiarrhythmic, antihypertensive or antianginal agents.

We claim:

1. A compound having Formula I,

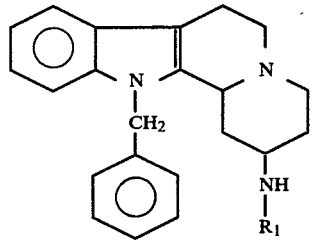

wherein $R_1$ is i-propyl, phenyl or a substituted phenyl having the structure

wherein $R_2$ is hydrogen, halogen, methoxy, lower alkyl, nitro, trifluoromethyl, acetamido, or sulfonamido; or a pharmacologically acceptable acid addition salt thereof.

2. The compound as in claim 1, wherein $R_1$ is i-propyl.

3. The compound as in claim 1, wherein $R_1$ is phenyl.

TABLE C

Influence of Indolquinolizines on Aortic-Coronary Sinus Difference in Oxygen Content in the Dog. Test Dose: 1 mg/kg, i.v.

| Compound | Arterio-Venous Difference in Oxygen Partial Pressure, mmHg, at | | | | | | | | |
|---|---|---|---|---|---|---|---|---|---|
| | 0 min | 1 min | 5 min | 10 min | 20 min | 30 min | 40 min | 50 min | 60 min |
| TR2981 | 31 | 17 | 20 | 21 | 22 | 23 | 24 | 24 | 24 |
| TR2998 | 23 | 12 | 16 | 18 | 17 | 18 | 17 | 19 | 20 |
| TR3006 | 45 | 30 | 44 | 45 | 42 | 37 | 38 | 36 | 36 |
| TR3008 | 26 | 20 | 23 | 22 | 23 | 25 | 25 | 24 | 25 |
| TR3014 | 32 | 17 | 18 | 26 | 25 | 26 | 26 | 26 | 24 |
| TR3631 | 37 | 26 | 33 | 32 | 30 | 30 | 32 | 31 | 31 |
| TR3633 | 41 | 31 | 35 | 39 | 39 | 36 | 36 | 36 | 38 |
| TR3635 | 28 | 24 | 24 | 24 | 23 | 24 | 26 | 25 | 26 |
| TR3687 | 21 | 15 | 22 | 23 | 20 | 20 | 20 | 23 | 23 |
| TR3698 | 28 | 27 | 27 | 27 | 28 | 28 | 29 | 28 | 27 |
| TR3716 | 27 | 22 | 27 | 29 | 28 | 27 | 28 | 28 | 28 |
| TR3718 | 23 | 20 | 17 | 17 | 16 | 16 | 16 | 18 | 18 |
| Nitroglycerin | 21 | 13 | 21 | 20 | 20 | 21 | 21 | 18 | 20 |

4. The compound as in claim 1, wherein $R_1$ is a substituted phenyl.

5. The compound as in claim 4, 12-benzyl-2-(3-nitroanilino)-1,2,3,4,6,7,12,12b-octahydroindolo[2,3-a]quinolizine.

6. The compound as in claim 4, 12-benzyl-2-(4-methoxyanilino)-1,2,3,4,6,7,12,12b-octahydroindolo[2,3-a]quinolizine dihydrochloride.

7. The compound as in claim 4, 12-benzyl-2-(3-methylanilino)-1,2,3,4,6,7,12,12b-octahydroindolo[2,3-a]quinolizine dihydrochloride.

8. The compound as in claim 4, 12-benzyl-2-(3-bromoanilino-1,2,3,4,6,7,12,12b-octahydroindolo[2,3-a]quinolizine hydrochloride.

9. The compound as in claim 4, 12-benzyl-2-(4-bromoanilino)-1,2,3,4,6,7,12,12b-octahydroindolo[2,3-a]quinolizine dihydrochloride.

10. The compound as in claim 4, 12-benzyl-1,2,3,4,6,7,12,12b-octahydro-2-(3-trifluoromethylanilino)indolo[2,3-a] quinolizine dihydrochloride.

11. The compound as in claim 4, 2-(4-acetamidoanilino)-12-benzyl-1,2,3,4,6,7,12,12b-octahydroindolo[2,3-a]quinolizine dihydrochloride.

12. The compound as in claim 4, 2-(3-acetamidoanilino-12-benzyl-1,2,3,4,6,7,12,12b-octahydroindolo[2,3-a]quinolizine oxalate.

13. The compound as in claim 4, 12-benzyl-1,2,3,4,6,7,12,12b-octahydro-2-(4-sulfonamidoanilino)-indolo[2,3-a]quinolizine hydrochloride.

14. A therapeutic method of treating cardiac arrhythmia in an individual for whom such therapy is indicated, comprising administering to the individual a therapeutically effective amount of a compound selected from the group consisting of 2-anilino-12-benzyl-1,2,3,4,6,7,12,12b-octahydroindolo[2,3-a]quinolizine dihydrochloride, 12-benzyl-2-(3-nitroanilino)-1,2,3,4,6,7,12,12b-octahydroindolo[2,3-a]quinolizine, 12-benzyl-2-(3-bromoanilino)-1,2,3,4,6,7,12,12b-octahydroindolo[2,3-a]quinolizine hydrochloride, 12-benzyl-2-(4-bromoanilino)-1,2,3,4,6,7,12,12b-octahydroindolo[2,3-a]quinolizine dihydrochloride, 12-benzyl-2-isopropylamino-1,2,3,4,6,7,12,12b-octahydroindolo[2,3-a]quinolizine dihydrochloride monohydrate, 2-amino-12-benzyl-1,2,3,4,6,7,12,12b-octahydroindolo[2,3-a]quinolizine dihydrochloride monohydrate.

15. A therapeutic method of treating hypertension in an individual for whom such therapy is indicated, comprising administering to the individual a therapeutically effective amount of a compound selected from the group consisting of 12-benzyl-2-(4-methoxyanilino)-1,2,3,4,6,7,12,12b-octahydroindolo[2,3-a]quinolizine dihydrochloride, 12-benzyl-2-(3-methylanilino)1,2,3,4,6,7,12,12b-octahydroindolo[2,3-a]quinolizine dihydrochloride, 2-(4-acetamidoanilino)-12-benzyl-1,2,3,4,6,7,12,12b-octahydroindolo[2,3-a]quinolizine dihydrochloride, 2-(3-acetamidoanilino)-12-benzyl-1,2,3,4,6,7,12,12b-octahydroindolo[2,3-a]quinolizine oxalate, 12-benzyl-1,2,3,4,6,7,12,12b-octahydro-2-(4-sulfonamidoanilino)-indolo[2,3-a]quinolizine hydrochloride.

16. A therapeutic method of treating angina pectoris in an individual for whom such therapy is indicated, comprising administering to the individual a therapeutically effective amount of a compound having the formula

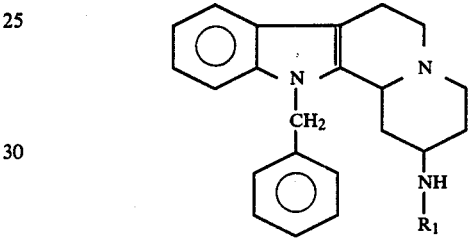

wherein $R_1$ is i-propyl, phenyl or a substituted phenyl having the structure

wherein $R_2$ is halogen, methoxy, lower alkyl, nitro, trifluoromethyl, acetamido or sulfonoamido; or a pharmacologically acceptable acid addition salt thereof.

* * * * *